(12) United States Patent
Van Es et al.

(10) Patent No.: US 6,693,209 B2
(45) Date of Patent: Feb. 17, 2004

(54) SYNTHESIS OF ANHYDROGLYCITOL ESTERS OF IMPROVED COLOUR

(75) Inventors: Daniël Stephan Van Es, Bennekom (NL); Augustinus Emmanuel Frissen, Wageningen (NL); Hendrikus Luitjes, Putten (NL)

(73) Assignee: ATO B.V., Wageningen (NL)

( * ) Notice: Subject to any disclaimer, the term of this patent is extended or adjusted under 35 U.S.C. 154(b) by 0 days.

(21) Appl. No.: 10/258,968

(22) PCT Filed: May 4, 2001

(86) PCT No.: PCT/NL01/00342

§ 371 (c)(1),
(2), (4) Date: Oct. 30, 2002

(87) PCT Pub. No.: WO01/83488

PCT Pub. Date: Nov. 8, 2001

(65) Prior Publication Data

US 2003/0114635 A1 Jun. 19, 2003

(30) Foreign Application Priority Data

May 4, 2000 (NL) .............................................. 1015119

(51) Int. Cl.[7] .............................................. C07C 57/00
(52) U.S. Cl. ........................ 554/229; 549/483; 549/484
(58) Field of Search .......................................... 554/229

(56) References Cited

FOREIGN PATENT DOCUMENTS

| EP | 0 052 295 | 5/1982 |
|----|-----------|--------|
| EP | 0 065 267 | 11/1982 |
| GB | 613444 | 11/1948 |
| WO | WO 99/45060 | 9/1999 |

OTHER PUBLICATIONS

Helmut et al. pp. 377–387, 1973.*
XP–002160510, PR. Nauk. Inst. Technol. Org. Tworzyw Sztucznych Politech. Wroclaw., Helmut et al., "Synthesis of some fatty acid esters in the presence of ion –exchange resins as catalysts", 1973, pp. 377–387.

* cited by examiner

Primary Examiner—Deborah Carr
(74) Attorney, Agent, or Firm—Young & Thompson

(57) ABSTRACT

Diesters of dianhydroglycitols can be prepared by esterification of dianhydroglycitols, anhydroglycitols and/or glycitols with alkylcarboxylic or arylcarboxylic acids in the presence of an acid catalyst, the acid catalyst being a macroporous acid ion exchange resin. If glycitols or monoanhydroglycitols are used as the starting material, the reaction temperature is initially of the order of 120° C. and after the dehydration is approximately 140° C.

12 Claims, No Drawings

SYNTHESIS OF ANHYDROGLYCITOL ESTERS OF IMPROVED COLOUR

This application is a 371 of PCT/NL01/00342 filed May 4, 2001.

The invention relates to an improved synthesis of alkyl and aryl esters of anhydroglycitol derivatives. These compounds are commercially interesting derivatives of the raw material sorbitol and other glycitols. The potential applications of these compounds are highly diverse. Esters of monoanhydrosorbitol (sorbitan) are widely used as emulsifiers (Span, Tween)[1, 2]. In addition, esters of dianhydrosorbitol (isosorbide) have many potential applications: as preservatives[3–5], lubricants[6], polymer stabiliser[7], emulsifier in cosmetics[8, 9], dispersing agents for pigments[10] or as plasticisers for vinyl resins[11–15].

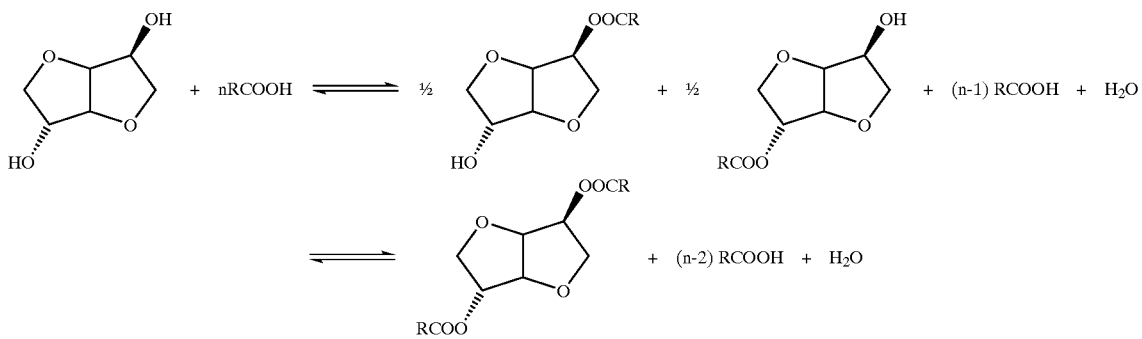

The dehydration of sorbitol, as an example of that of the glycitols, is shown in the diagram below:

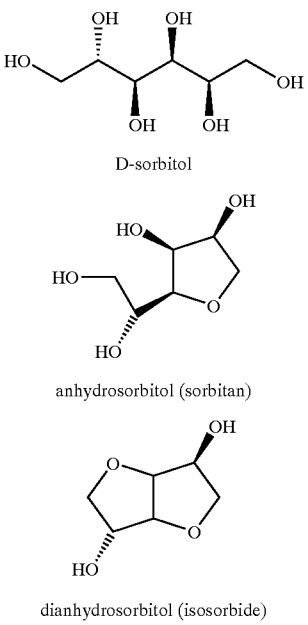

The current synthesis methods are usually based on acid-catalysed direct esterifications, sulphuric acid or p-toluenesulphonic acid being used as catalyst[13,14]. Base-catalysed reactions are also known; however, the reactions concerned here are usually transesterification reactions at high temperature (above 200° C.)[16–18]. Furthermore, the use of acid ion exchange resins of the gel type as catalyst is also reported[19,20]; in this context yields of 61 and 63% for isosorbide dibutyrate and isosorbide dipropionate, respectively, are reported, starting from isosorbide.

In the case of the direct esterification the reaction equilibrium is shifted by removal of the water of reaction. This can be achieved by azeotropic distillation with toluene or xylene[13,14,20], or by the use of a vacuum[21]. Yields in excess of 70% diester, starting from isosorbide, are not achieved with any of the above-mentioned methods.

The esterification of isosorbide is shown in the following equation:

The invention relates to the synthesis of esters of dianhydrosorbitol and other dianhydroglycitols with high conversion (98–100%) and a substantially improved colour, as a result of which distillation of the product can be dispensed with. According to the invention use is made of a macroporous acid ion exchange resin as catalyst. In addition, an inert gas, such as nitrogen gas, is preferably dispersed through the reaction mixture in order to accelerate the removal of the water of reaction. A further improvement is obtained by increasing the turbulence of the reaction mixture, so that the removal of the water of reaction is further promoted. A reduced pressure of, for example, 10–50 mbar is also advantageous. The colour of the reaction mixture is substantially improved because the reaction temperature can be kept below 150° C. Furthermore, addition of activated charcoal to the reaction mixture leads to a further reduction in the colour.

In addition to dianhydrosorbitol (isosorbide) as starting material it has also proved possible to use anhydrosorbitol (sorbitan) and even sorbitol as starting material. If the reaction temperature in the initial stage of the reaction is kept low (120–125° C.), selective dehydration takes place, followed by esterification after raising the reaction temperature to 140–150° C. Giacometti et al.[22,23] merely reported the possibility of in situ formation of anhydrosorbitol derivatives during the esterification of sorbitol with p-toluenesulphonic acid, without specifying experimental details for this.

Although ion exchange resins have been used as catalyst in the reaction for the dehydration[19,21,24] of sorbitol, the conversions were too low (39–57%) and the reaction times usually too long (2–24 hours). Feldmann et al. (DE 3 041 673) reported the dehydration of sorbitol with the aid of a macroporous ion exchange resin, the water of reaction being removed with the aid of a stream of nitrogen. Despite the high yield of isosorbide (93%), the reaction mixture was severely discoloured and the reaction time was long (5 h).

Matyschok et al.[21] also reported the synthesis of isosorbide esters with the aid of an acid ion exchange resin of the gel type (Wofatit KPS), in which context it must be mentioned that the alkanoic acids used by them have a short chain and thus high intrinsic acidity (acetic acid, propionic acid, butyric acid). The reported yields are, however, too low to be of industrial relevance (60–70%).

The process according to the invention preferably relates to the synthesis of diesters in accordance with the following equation:

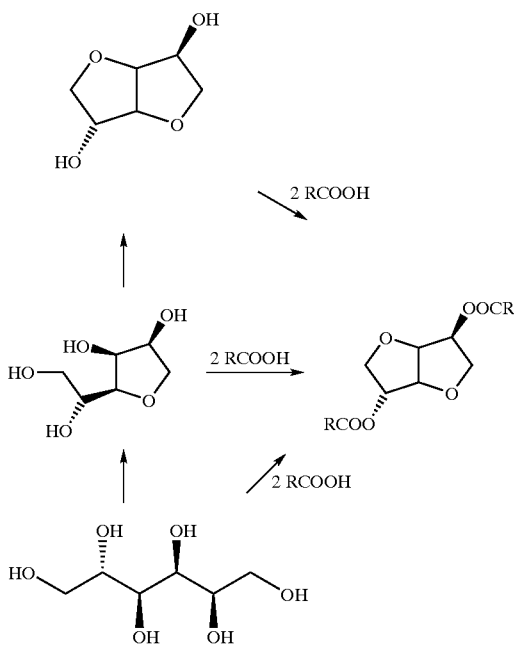

Surprisingly it has been found that a substantially improved method of preparation for dianhydrosorbitol diesters has been developed by a combination of techniques known per se. In view of the increasing industrial relevance of dianhydrosorbitol diesters, this meets an important need.

The process according to the invention can be used for the esterification of glycitols and the monoanhydro and dianhydro derivatives thereof. A glycitol is understood to be a sugar alcohol having at least 6 carbon atoms. These include, first of all, sorbitol, mannitol, iditol and other hexitols, but also higher analogues such as heptitols and glycitols derived from the di- and oligo-saccharides, such as lactitol, maltitol, and the like. The process according to the invention can also be used for glycitols (sugar alcohols) that cannot be converted to dianhydro analogues, such as pentitols (xylitol, etc.), in which case diesters and higher esters of the monoanhydro analogues (xylitan, etc.) are then formed.

The esterification can take place with any carboxylic acid, such as alkanoic acids, alkenoic acids, alkadienoic acids, cycloalkanecarboxylic acids and arenecarboxylic acids. The carboxylic acids can be either straight-chain or branched. Examples are propionic acid, hexanoic acid, octanoic acid, nonanoic acid, decanoic acid, lauric acid, stearic acid, cyclohexanecarboxylic acid, optionally substituted benzoic acids, phenylacetic acid, naphthalenecarboxylic acid, etc. The diesters of $C_3$–$C_{20}$ carboxylic acids are particularly advantageous. Mixtures of acids, in particular fatty acids of varying chain length, can also be used.

The esters of shorter chain carboxylic acids, such as $C_3$–$C_6$, can be used in the main as solvents, those of medium chain length alkanoic acids, in particular of $C_6$–$C_{12}$ carboxylic acids, are outstandingly suitable as plasticisers and the longer chain length, for example $C_{12}$–$C_{18}$, carboxylic acids are mainly usable as lubricants. If desired, monoesters of dianhydroglycitols can also be obtained by using smaller amounts of fatty acids, for example 1 to 2 mol per mol (anhydro)glycitol. What is concerned in this case is then mainly the preparation of emulsifiers, such as the monoesters of $C_{12}$–$C_{20}$ alkanoic acids or alkenoic acids and monoaryl and monoaralkyl esters.

The choice of the catalyst resin is important. This is an acid catalyst resin of the macroporous or macroreticular type. In contrast to resins of the gel type, these are resins with a relatively high degree of crosslinking and consequently a high porosity. A description of suitable resins is to be found in standard works on catalyst resins, such as "Ion Exchangers" by Konrad Dörfner, published by De Gruyter, Berlin, 1991, in particular pages 22–23 thereof. Examples of suitable resins are the commercially available resins, such as Amberlyst-15-wet, Amberlyst-15-dry, Amberlyst-16-wet and Amberlyst-36-dry from Rohm and Haas, and comparable resins from other suppliers.

EXAMPLES

General Procedure

The reaction was carried out in a 2.0 l four-necked, round-bottomed flask equipped with a gas inlet tube (with glass frit), a Pt-100 temperature sensor, a Dean-Starck condenser and a mechanical stirrer. The mechanical stirrer was equipped with a stainless steel centrifugal stirrer (60 mm diameter). Stirring was carried out at a speed of 900 revolutions per minute. Heating of the reactor was achieved using an Isopad 2.0 l electrical heating jacket, equipped with a temperature control unit. During the reaction nitrogen gas was dispersed through the reaction mixture via a gas inlet tube at a flow rate of 400 ml per minute. The progress of the reaction was followed both by measuring the quantity of water formed over time and by GLC determination of the reaction mixture. After complete conversion had been achieved, the reaction mixture was cooled to approximately 60–80° C., after which the catalyst was removed by means of a sieve. The reaction mixture was then stirred for some time (0.5–1.5 hours) with active charcoal at 80–100° C. Filtration of this mixture through a glass filter with Filteraid yielded a pale yellow viscous mixture of isosorbide diester and alkanoic acid. The excess alkanoic acid was then removed by means of vacuum distillation. GLC and $^{13}C$ NMR analysis (of both the product and the hydrolysed product) of the product thus obtained showed only the presence of the desired isosorbide diester. Average isolated yields were between 95 and 99%.

Example 1

Synthesis of Isosorbide 2,5-di-n-octanoate Using Isosorbide as the Starting Material A mixture of isosorbide (292.3 g, 2.00 mol), n-octanoic acid (865.3 g, 6.00 mol, 3 eq) and 40 g Amberlyst 15 (dry) resin was stirred at a constant temperature (see Table 1). After complete conversion had been achieved, the yellow transparent reaction mixture was decolourised with active charcoal. The excess n-octanoic acid was then distilled off under vacuum. The product was a pale yellow transparent viscous liquid (95–98%).

TABLE 1

Esterification of isosorbide with n-octanoic acid: reaction times at complete conversion

| isosorbide (mol) | acid (eq) | T (° C.) | reaction time (hours) | colour |
|---|---|---|---|---|
| 1 | 5 | 145 | 6 | pale yellow |
| 2 | 3 | 120 | 11 | yellow |
| 2 | 3 | 145 | 7 | yellow |

Example 2

Synthesis of Isosorbide 2,5-di-2-ethylhexanoate Using Isosorbide as the Starting Material A mixture of isosorbide (292.3 g, 2.00 mol), 2-ethylhexanoic acid (865.3 g, 6.00 mol, 3 eq) and 40 g Amberlyst 15 (dry) resin was stirred at a constant temperature (see Table 2). After complete conversion had been achieved, the yellow transparent reaction mixture was decolourised with active charcoal. The excess 2-ethylhexanoic acid was then distilled off under vacuum. The product was a pale yellow transparent viscous liquid (95–98%).

TABLE 2

Esterification of isosorbide with 2-ethylhexanoic acid: reaction times at complete conversion

| isosorbide (mol) | acid (eq) | T (° C.) | time (hours) | colour |
|---|---|---|---|---|
| 1 | 5 | 145 | 13 | yellow |
| 2 | 3 | 145 | 12 | pale yellow |
| 2 | 3 | 160 | 6 | yellow |

Example 3

Synthesis of Isosorbide 2,5 di-n-octanoate Using 1,4-sorbitan as the Starting Material A mixture of 1,4-sorbitan, (164.5 g, 1.00 mol), n-octanoic acid (432.7 g, 3.00 mol, 3 eq) and 20 g Amberlyst 15 (dry) resin was stirred at 145° C. Complete conversion was achieved after 8 hours. After removal of the catalyst, the yellow transparent reaction mixture was decolourised with active charcoal. $^{13}$C NMR analysis of the hydrolysed product of the reaction mixture indicated only the formation of isosorbide dioctanoate. Distilling off the excess n-octanoic acid, followed by a second decolourisation, gave a pale yellow product in a yield of 80%.

Example 4

Synthesis of Isosorbide 2,5 di-n-octanoate Using sorbitol as the Starting Material A mixture of sorbitol, (364.34 g, 2.00 mol), n-octanoic acid (865.3 g, 6.00 mol, 3 eq) and 40 g Amberlyst 15 (dry) resin was stirred at 125° C. After approximately 4 mol water had been collected (indicative of quantitative dehydration), the temperature was raised to 145° C. Complete conversion was achieved after 8 hours. After removal of the catalyst, the yellow-brown transparent reaction mixture was decolourised with active charcoal. $^{13}$C NMR analysis of the hydrolysed product of the reaction mixture indicated only the presence of isosorbide dioctanoate.

Example 5

Synthesis of Isosorbide 2,5 di-n-octanoate Using Isosorbide and Active Charcoal as the Starting Materials A mixture of isosorbide (292.3 g, 2.00 mol), n-octanoic acid (865.3 g, 6.00 mol, 3 eq), 40 g Amberlyst 15 (dry) resin and 20 g active charcoal was stirred at 145° C. After complete conversion had been achieved, the reaction mixture was filtered. The excess n-octanoic acid was then removed from the resulting pale yellow reaction mixture by means of distillation. After adding n-hexane and further active charcoal (10 g) thee product was stirred for a further 1 hour at 80° C. Removal of the charcoal by filtration, followed by removal of the n-hexane (under reduced pressure), yielded a virtually "after-white" product.

LITERATURE REFERENCES

1) Kobayashi T.; Mori, N.; Nishida, M.; Isobe, K.; Iwasaki, R. Surface active agent composition; Lion Corp.: Japanese Patent Application JP-A-8-173787, 1996.
2) Kobayashi T.; Mori, N.; Iwasaki R. Draining agent and draining method; Lion Corp.: Japanese Patent Application JP-A-8-281003, 1996.
3) Amano, H.; Yoshida, C.; Nakamura, A. Chem. Abstr. 1980, 93, 69076.
4) Knightly, W. H. Preparation of baked goods; Atlas Chemical Industries: U.S. Pat. No. 3,394,009, 1968.
5) Rusch, D. T. Chem. Abstr. 1971, 75, 117364
6) Hughes, F. A. Preventing blocking of aluminium sheets; Atlas Chemical Industries: U.S. Pat. No. 3,468,701, 1969.
7) Stephen, J. F.; Smith, J. H.; Meshreki, M. H. Hindered phenolic compounds derived from hexides as stabilizers; ICI Americas Inc: U.S. Pat. No. 4,613,638, 1986.
8) Ochiai, M.; Ozawa, T. Chem. Abstr. 1979, 90, 209946.
9) Kazuhisa, F. Cosmetics containing isosorbide fatty acid diesters; Nihon Surfactants Co.: Japanese Patent Application JP-59-125408, 1984.
10) anonymous Res. Discl. 1977, 158, 45–47.
11) Braun, D.; Bergmann, M. Angew. Macromol. Chem. 1992, 199, 191–205.
12) Le Maistre, J. W.; Ford, E. C. Epoxidized diesters of polyoxyethylene isosorbide; Atlas Chemical Corporation: U.S. Pat. No. 3,225,067, 1965.
13) MacKay Bremner, J. G.; Beaumont, S. Improvements in and relating to the production of heterocyclic compounds; ICI, British Patent 613,444, 1946.
14) Hayashi Kogyo Kagaku zasshi 1953, 56, 623–625.
15) Luitjes, L.; Jansen, J. Bicyclooctane derivatives as plasticisers; ATO-DLO: International Patent Application WO 99/45060 (PCT/NL99/00115).
16) Prossel, G.; Papenfuhs, B. Verfahren zur Herstellung von Mischungen aus Sorbitmonoestern, Sorbitdiestern und Partialglyceriden (Process for the preparation of mixtures of sorbitol monoesters, sorbitol diesters and partial glycerides); Clariant GmbH: European Patent Application EP 0 889 023 A1, 1999.
17) Stuehler, H.; Kremp, E.; Oberhauser, A. Anhydroghexitol carboxylic acid esters; Hoechst A G, German Patent Application DE 3119 553, 1982.
18) Stockburger, G. J. Process for preparing sorbitan esters; ICI Americas Inc: U.S. Pat. No. 4,297,290, 1981.
19) Goodwin, J. C.; Hodge, J. E.; Weisleder, D. Carbohydrate Res. 1980, 79, 133–141.
20) Matyschok, H.; Ropuszynski, S. Pr. Nauk. Inst. Technol. Org. Tworzyw. Sztucznych Polytech. Wroclaw, 1973, 13, 377–387.

21) Fleche, G.; Huchette, M. Starch 1986, 26–30.
22) Giacometti, J.; Wolf, N.; Gomzi, Z.; Milin, C. React. Kinet. Catal. Lett. 1996, 59, 235–240.
23) Giacometti, J.; Milin, C.; Wolf, N.; Giacometti, F. J. Agric. Food Chem. 1996, 44, 3950–3954.
24) Bock, K.; Pedersen, C.; Thogersen, H. Acta Chem. Scand. 1981, B 35, 441–449.

What is claimed is:

1. A process for the preparation of esters of (di)anhydroglycitols by esterification of dianhydroglycitols, anhydroglycitols and/or glycitols with alkylcarboxylic or arylcarboxylic acids containing 3 to 18 carbon atoms in the presence of an acid catalyst, characterised in that the acid catalyst is a macroporous acid ion exchange resin, and the molar ratio of carboxylic acid to ((di)anhydro)glycitol is selected between 2 and 5.

2. A process according to claim 1, wherein the molar ratio of carboxylic acid to ((di)anhydro)glycitol is selected between 2 and 3.

3. A process according to claim 1, wherein the water of reaction is removed by passing a stream of inert gas through the reaction mixture.

4. A process according to claim 1, wherein the reaction temperature is between 120° C. and 180° C., in particular between 120° C. and 150° C.

5. A process according to claim 1, wherein a sulphonic acid ion exchange resin of the styrene-divinylbenzene copolymer type is used.

6. A process according to claim 5, wherein a macroporous ion exchange resin of the Amberlyst type is used.

7. A process according to claim 1, wherein the carboxylic acids contain 5 to 14 carbon atoms.

8. A process according to claim 1, wherein the dianhydroglycitol is isosorbide.

9. A process according to claim 1, wherein the anhydroglycitol is 1,4-sorbitan, 2,5-sorbitan or 3,6-sorbitan, or a mixture of sorbitan isomers.

10. A process according to claim 1, wherein sorbitol is esterified.

11. A process according to claim 1, wherein a glycitol or monoanhydroglycitol is esterified and the reaction temperature is kept between 120° C. and 130° C. during the dehydration reaction of the glycitol (first step) and the reaction temperature is raised to 130° C. to 160° C. after the dehydration reaction.

12. A process according to claim 1, wherein the reaction is carried out with active charcoal in the reaction mixture.

* * * * *